(12) United States Patent
Powlan

(10) Patent No.: US 8,337,495 B1
(45) Date of Patent: Dec. 25, 2012

(54) DISTAL LOCKING INTRAMEDULLARY NAIL

(76) Inventor: Roy Y. Powlan, Lafayette, CA (US)

( * ) Notice: Subject to any disclaimer, the term of this patent is extended or adjusted under 35 U.S.C. 154(b) by 0 days.

(21) Appl. No.: 13/136,959

(22) Filed: Aug. 16, 2011

(51) Int. Cl.
*A61B 17/56* (2006.01)
*A61B 17/58* (2006.01)
*A61F 2/30* (2006.01)

(52) U.S. Cl. ............... 606/63; 606/62; 606/64; 606/68

(58) Field of Classification Search .............. 606/62–68, 606/86 A, 246–279
See application file for complete search history.

(56) References Cited

U.S. PATENT DOCUMENTS

| | | | |
|---|---|---|---|
| 3,759,257 A * | 9/1973 | Fischer et al. | ................... 606/63 |
| 4,204,531 A | 5/1980 | Aginsky | |
| 4,227,518 A | 10/1980 | Aginsky | |
| 4,519,100 A | 5/1985 | Wills | |
| 4,858,602 A | 8/1989 | Seidel | |
| 5,057,103 A | 10/1991 | Davis | |
| 5,458,599 A | 10/1995 | Adobbati | |
| 5,810,820 A | 9/1998 | Santori et al. | |
| 6,077,264 A | 6/2000 | Chemello | |
| 6,558,388 B1 | 5/2003 | Bartsch et al. | |
| 6,575,973 B1 | 6/2003 | Shekalim | |
| 6,736,818 B2 | 5/2004 | Perren | |
| 7,052,498 B2 | 5/2006 | Levy | |
| 7,601,152 B2 | 10/2009 | Levy et al. | |
| 7,632,277 B2 | 12/2009 | Woll | |
| 2008/0195098 A1 * | 8/2008 | Gotfried | .................. 606/62 |

OTHER PUBLICATIONS

Mismatch of current intramedullary nails with the anterior bow of the femur,Dr.K.A.Egol et al,Journal of Orthopedic Trauma,Aug. 18, 2004,(7) p. 410-5, Pub Med,US Nat.Lib.of Med.

* cited by examiner

*Primary Examiner* — Eduardo C Robert
*Assistant Examiner* — Nicholas Plionis

(57) ABSTRACT

The nail is inserted into the interior of a long tubular bone. It has a plurality of elongate segments joined to the leading end of its tubular sheath. When the segments are urged through a segment guiding device that is positioned at the leading end of the sheath, the segments with their sharpened bone penetrating distal ends exit in a radial distal direction causing them to lock into the surrounding bone. During the distal translation of the sheath and the elongate segments, the segment guiding means is maintained in a fixed position relative to the surrounding bone by the centrally placed shaft of a setting tool.

7 Claims, 5 Drawing Sheets

FIG. 12
FIG. 13
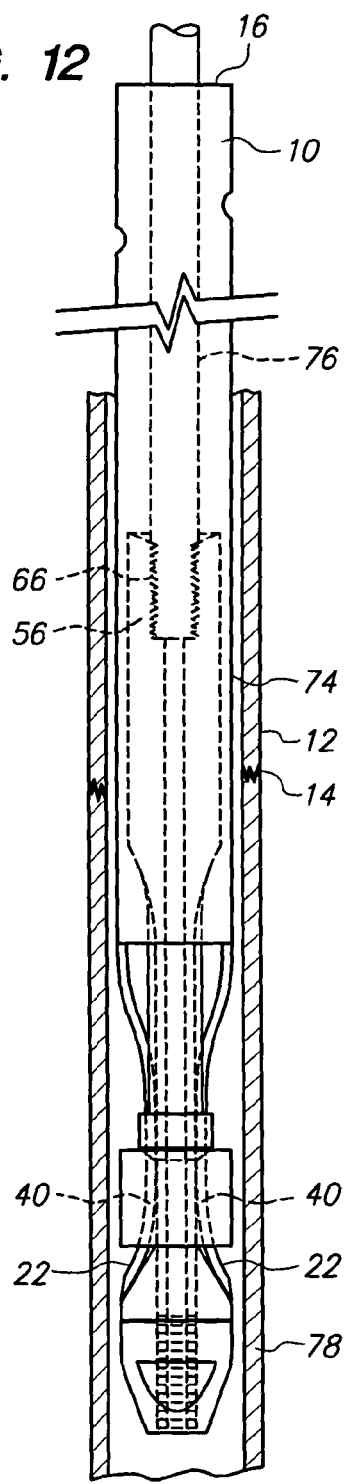
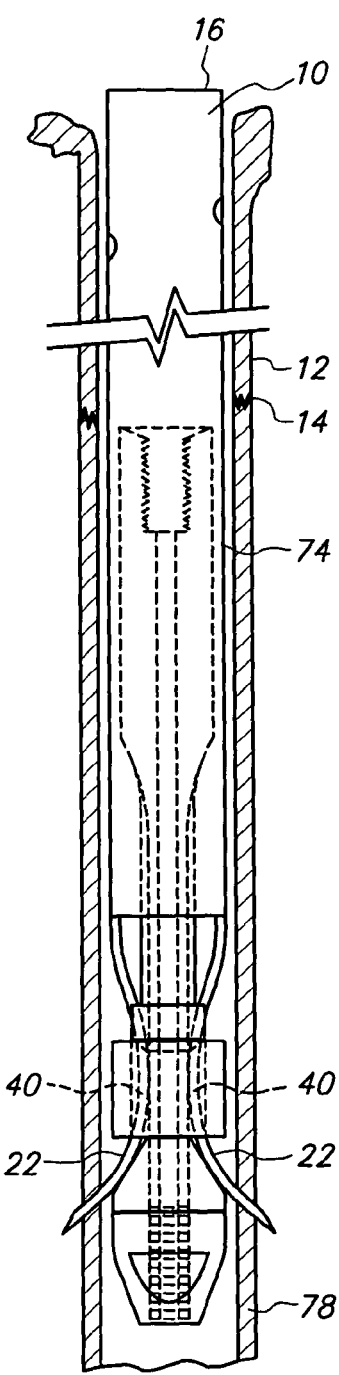

DISTAL LOCKING INTRAMEDULLARY NAIL

BACKGROUND

Prior Art

The following is a tabulation of some prior art that presently appears to be relevant:

U.S. patents.

| Pat. No. | Kind Code | Issue Date | Patentee |
| --- | --- | --- | --- |
| 5,810,820 | B1 | Sep. 22, 1998 | Santorini et al. |
| 6,558,388 | B1 | May 06, 2003 | Bartsch |
| 7,601,152 | B2 | Oct. 13, 2009 | Levy et al. |

Non-Patent Literature Documents

Mismatch of current intramedullary nail with the anterior bow of the femur.

Dr. Egol K A, et al, Journal of Orthopedic Trauma, 2004, Aug. 18(7); 410-5

FIELD OF THE INVENTION

This invention relates generally to the fixation of fractured bones having an intramedullary canal such as the femur, to which the following description refers to purely by way of example.

BACKGROUND AND RELATED TECHNOLOGY

The treatment of choice for uncomplicated fractures of long tubular bones, the femur for example, is intramedullary nailing, in which a generally tubular rod, commonly referred to as a nail is introduced into the medullary cavity of a bone, most often from the proximal or hip end, usually over a guide wire that had been inserted to help align the fracture and to guide the nail across the fracture into the distal end of the bone. When the fracture is unstable, broken into several pieces for example, and tending to telescope and cause shortening of the limb, it is necessary to stabilize the fracture even more by placing screws transversely through orifices at both ends of the nail to fasten the nail to the bone. The orifices at the proximal end of the nail are relatively easy to locate, but it is very difficult to locate those at the distal end of the nail, hidden as they are deep within the medullary canal, muscles and soft tissue. Because of this difficulty, there have been numerous attempts to invent nails that are self-locking at their distal ends to avoid the need for the distal transverse locking screws. Because of the stringent requirements for a successful self-locking nail, very few have achieved widespread acceptance.

Some examples of self-locking nails are; Aginsky in which the distal end of the nail comprises leg-like means that in use, are spread apart by a wedge, to engage with the inner surface of the osseous canal. Also Aginsky U.S. Pat. No. 4,204,531 uses small lever arms instead of a wedge to spread the legs of the distal nail. Fischer, U.S. Pat. No. 3,760,802, and Adobbati, U.S. Pat. No. 5,458,599 use a similar centrally located means to spread and radially enlarge a device at the distal end of the sheath causing it to press against the inner surface of the osseous canal to achieve a friction grip. This type of friction engagement with the wall of the canal is usually inadequate to resist the axial and rotational forces associated with full weight bearing. In addition, the presence of centrally located actuating mechanisms precludes the use of guide wires and the use of prior art proximally placed transfixing screws, and also precludes the use of a nail that is curved to match the natural anterior curvature of the femur. Another type of distal locking nail employs small blades or splines that are deployed from within a tubular nail to engage with the osseous canal wall. Examples are Wills, U.S. Pat. No. 4,519,100, Davis U.S. Pat. No. 5,057,103, Chemello, U.S. Pat. No. 6,077,264, and Shekalim, U.S. Pat. No. 6,575,973.

Levy, U.S. Pat. No. 7,052,498, and Levy, U.S. Pat. No. 7,601,152, describe a nail in which the proximal and distal ends of the nail sheath are comprised of umbrella-like ribs that are caused to expand and press against the interior surface of the medullary canal by means of a central actuating device. The fragile ribs provide little resistance to axial and rotational forces and subsequent bone ingrowth would prevent re-folding of the ribs making removal of the nail very difficult.

Examples of distal fixation by means of radial expansion of distal sheath segments are Seidel, U.S. Pat. No. 4,858,602, Perren, U.S. Pat. No. 6,736,818, and Woll, U.S. Pat. No. 7,632,277. These segments press against but do not penetrate into the osseous canal, again providing little resistance to axial and rotational forces. Further, bone in-growth onto the segments would tend to prevent collapse of the segments, making removal of the nail very difficult.

Devices that achieve distal fixation by means of individual wires which are deployed from within the tubular nail sheath, the ends of which penetrate into the wall of the canal are Santorini, U.S. Pat. No. 5,810,820, and Bartsch, U.S. Pat. No. 8,558,388.

SUMMARY OF THE INVENTION

An object of this invention is a nail in which the locking elements do not merely press against the inner surface of the medullary canal to achieve fixation, but are strongly driven directly into the walls of the canal, either the hard cortical bone at the middle of the shaft, or into the softer cancellous bone at both ends, and as a result, the nail is able to resist axial and rotational forces.

A further object is a nail that can easily removed after healing has taken place despite the growth of new bone in and around the distal end of the nail.

A further object is a nail that is free of a centrally located deployment mechanism that would preclude the use of a curved nail, or the use of prior art proximal transfixing screws. It would also permit a central cannulation for the use of a guide wire, an important consideration.

A further object is a nail that is free of small pivots, pivot pins, levers, splines or fragile blades that can bend, break or jam during the insertion or removal of the nail This invention achieves these objectives through a concept of distal fixation that is not taught by the prior art. The nail comprises an elongate generally cylindrical tubular rod with a proximal end and a distal end. The distal end of the sheath comprises a plurality of circumferentially disposed elongate sheath segments which are positioned within the channels of a segment guiding means, the means being located at the distal end of the nail, and partially and slidingly within the lumen of the distal sheath. To achieve locking of the nail after it has been positioned within the medullary canal in the usual manner, a setting tool with an elongate shaft is releasably attached to the proximal end of the segment guiding means and is used to maintain the segment guiding means in a fixed position relative to the surrounding wall of the medullary canal, during the time that the nail sheath is being urged further in a distal direction, and as a result of this further distal translation of the sheath, the distal sheath segments are translated through the forming channels of the segment guiding means to emerge from them in a radial-distal direction, and penetrate into the walls of the surrounding osseous canal, resulting in a strong, reversible locking of the distal end of the nail to the bone.

An advantage of the use of prepared segments of the distal nail sheath itself as a method of fixation is that the segments made from the sheath can be made generally thicker, wider and stronger than fixation means that are deployed from within the sheath which are constrained in size and configuration by the limited volume of the distal sheath. The penetration of the prepared distal ends of the distal sheath segments into the encircling bone results in a strong positive locking in contrast with the prior art that merely presses against the canal wall, or uses small individual blades.

A further advantage of this method of locking is that the radial distal direction of the segments when deployed into the surrounding bone presents with a much greater resistance to axial shearing forces than do the usual transversely placed threaded locking screws, that have broken in the past, leading to very difficult surgery for their removal.

In a preferred embodiment, the nail comprises an elongate, generally cylindrical tubular sheath with a proximal end and a distal end, the proximal end comprising a means for the insertion of a known transfixing screw, and with the distal end comprising two circumferentially disposed and radially opposed elongate sheath segments of predetermined length and width, with the distal end of each segment having a shaped bone penetrating cutting means, and with each segment positioned at, and slidingly partially within a channel of the segment guiding means, while in a retracted position, prior to the deployment of the segments into the surrounding bone.

In another embodiment, the distal sheath comprises three elongate segments equally spaced around the circumference of the sheath, and with the distally located segment guiding means comprised of three circumferentially spaced channels.

In yet another embodiment, the distal sheath comprises four elongate segments equally spaced around the circumference of the sheath, and with the distally located segment guiding means comprised of four circumferentially spaced channels.

In another embodiment, the segment guiding means is not centrally cannulated, permitting the use of very small diameter nails for use in bones with narrow medullary canals.

BRIEF DESCRIPTION OF THE DRAWINGS

The preset invention is illustrated by way of example, and not by way of limitation, in the figures of the accompanying drawings, in which:

FIG. 12 is a partially sectioned frontal view of the nail with a fragment of the shaft of a setting tool attached to the segment guiding means, prior to deployment in a narrow osseous canal.

FIG. 13 is a partially sectioned frontal view of the nail after deployment in cortical bone, and before insertion of a known proximal transfixing screw. The shaft of a setting tool has been removed.

DETAILED DESCRIPTION OF THE DRAWINGS

Figure 1:
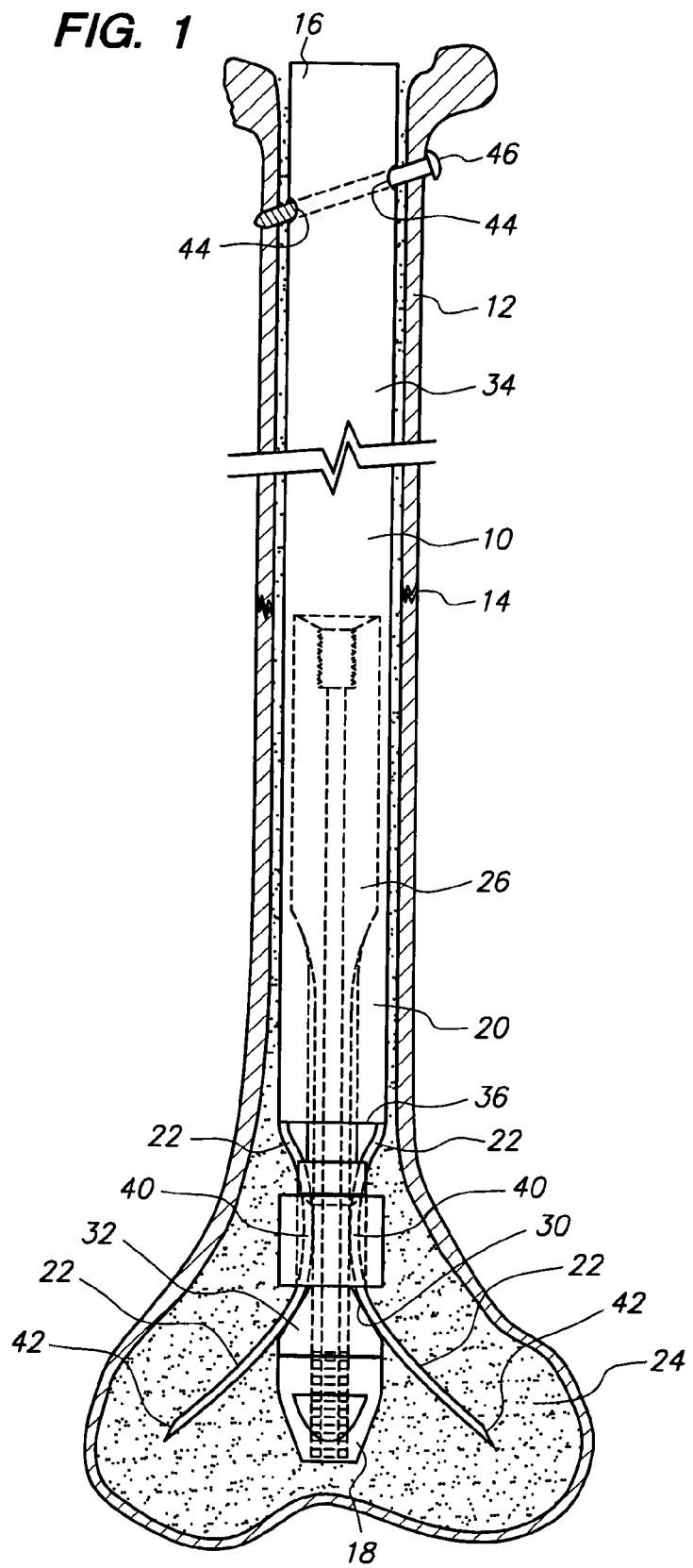
FIG. 1 is a partially sectioned perspective view showing the locking segments fully deployed in cancellous bone at its distal end.

For convenience, the same or equivalent elements in the various embodiments of the invention illustrated in the drawings have been identified with the same reference numerals. Further, in the description that follows, any reference to exact dimensions, or particular construction materials shown herein are examples of suitable configurations only, and not intended to be limiting in any way. Depending on the needs of the particular application, those skilled in the art will readily recognize, in light of the following teachings, a great many suitable alternative implementation details. In the following description, any reference to orientation or direction is intended solely for the convenience of description and is not intended in any way to limit the scope of the present invention.

FIG. 1 shows one embodiment of the nail within the tubular bone 12, with a fracture 14.

In this embodiment, the nail 10 has a proximal end 16 and a distal end 18 and a generally tubular body 20. Its distal end comprises two radially opposed segments, 22 and 22, each comprising at least a quarter of the circumference of the distal sheath, and each being of a predetermined length so that when deployed, they extend into the bone, cortical or cancellous 24 as shown in FIG. 1, a sufficient distance to achieve locking. In one embodiment, the length of the segments 22 of a 13 mm. diameter nail measures 50 mms. It would be obvious to one skilled in the art that the exact configuration of the segments would vary, depending on such factors as the number of segments, whether the segment is to be locked in cortical or cancellous bone, the diameter of the nail, the thickness of the distal sheath wall, the construction material, i.e. stainless steel or other biocompatible material, whether preformed and spring tempered or annealed, to name only a few factors.

It would also be obvious to one skilled in the art that the nail sheath 20 shown as tubular in this embodiment could have a number of cross-sections other than tubular at different levels of the nail, such as clover leaf for example, the sheath could be curved to match the natural curvature of a bone, and the sheath could be slotted through its length, or partially so.

FIG. 1 shows the nail fully deployed in the cancellous bone 24 of an illustrative femur near its distal end 18. The segment guiding means 26 is shown located at, and partially within the distal lumen 28 of the nail sheath. Two distal sheath segments 22 are shown entering and exiting the channels 40 of the segment guiding means 26 and have been redirected into a radial distal direction by the bevels 30 of the segment deflector sleeve 32.

Figure 2:
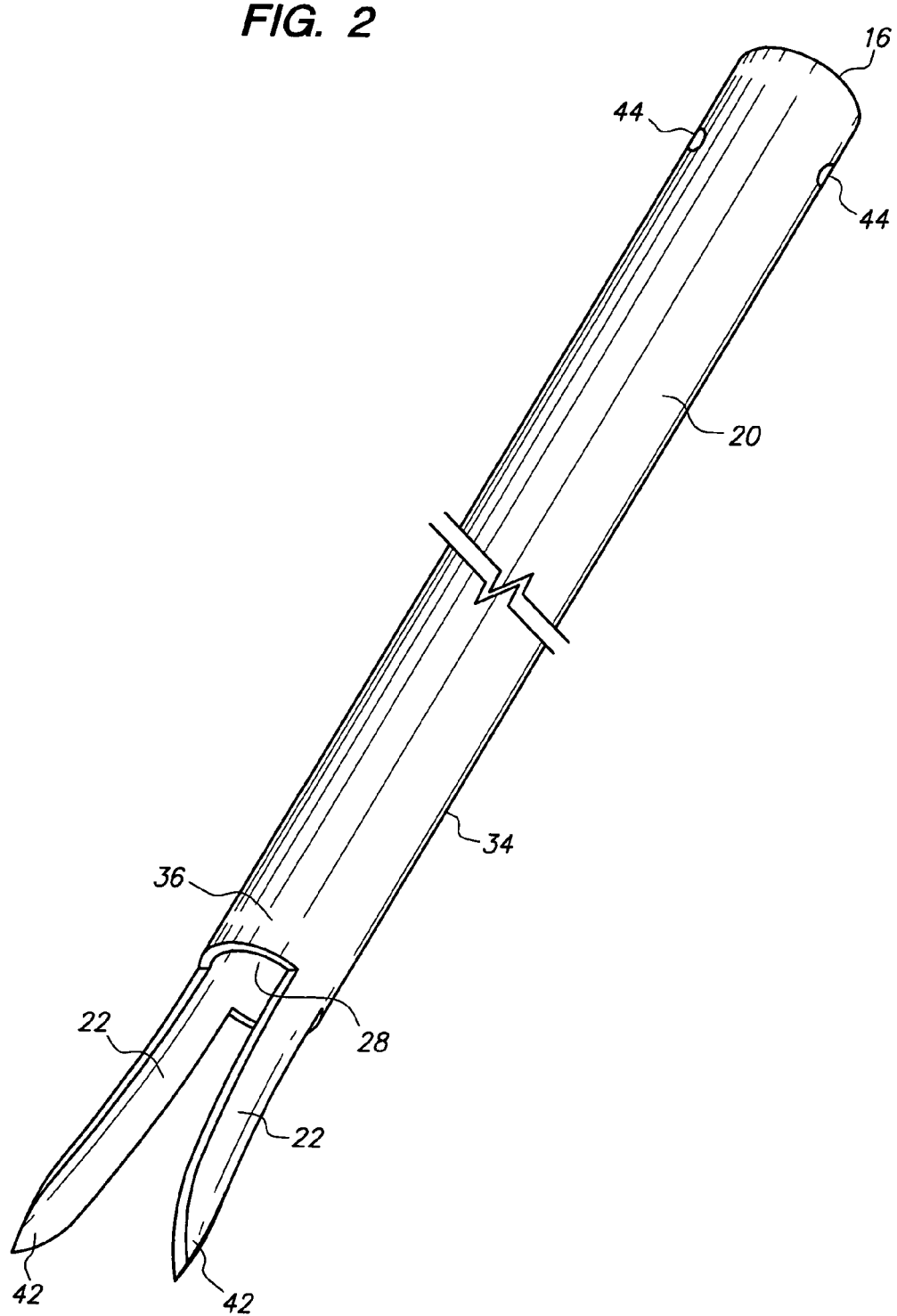
FIG. 2 is a perspective view of the nail sheath showing two integral prepared elongate distal segments, and with the proximal end showing prior art openings for a known transfixing screw.

FIG. 2 shows an embodiment of the nail sheath prior to its assembly with the segment guiding means 26 within its distal end 36. This embodiment comprises an elongate tubular sheath 20, with two prepared radially symmetrical circumferentially disposed elongate distal sheath segments 22, each shaped to have a sliding fit within the elongated grooves 38 and the channels 40 of the segment guiding means 26. The distal end of each segment comprises a bone penetrating cutting means 42. The orifices 44 permit the insertion of a known transfixing screw 46.

Figure 3:
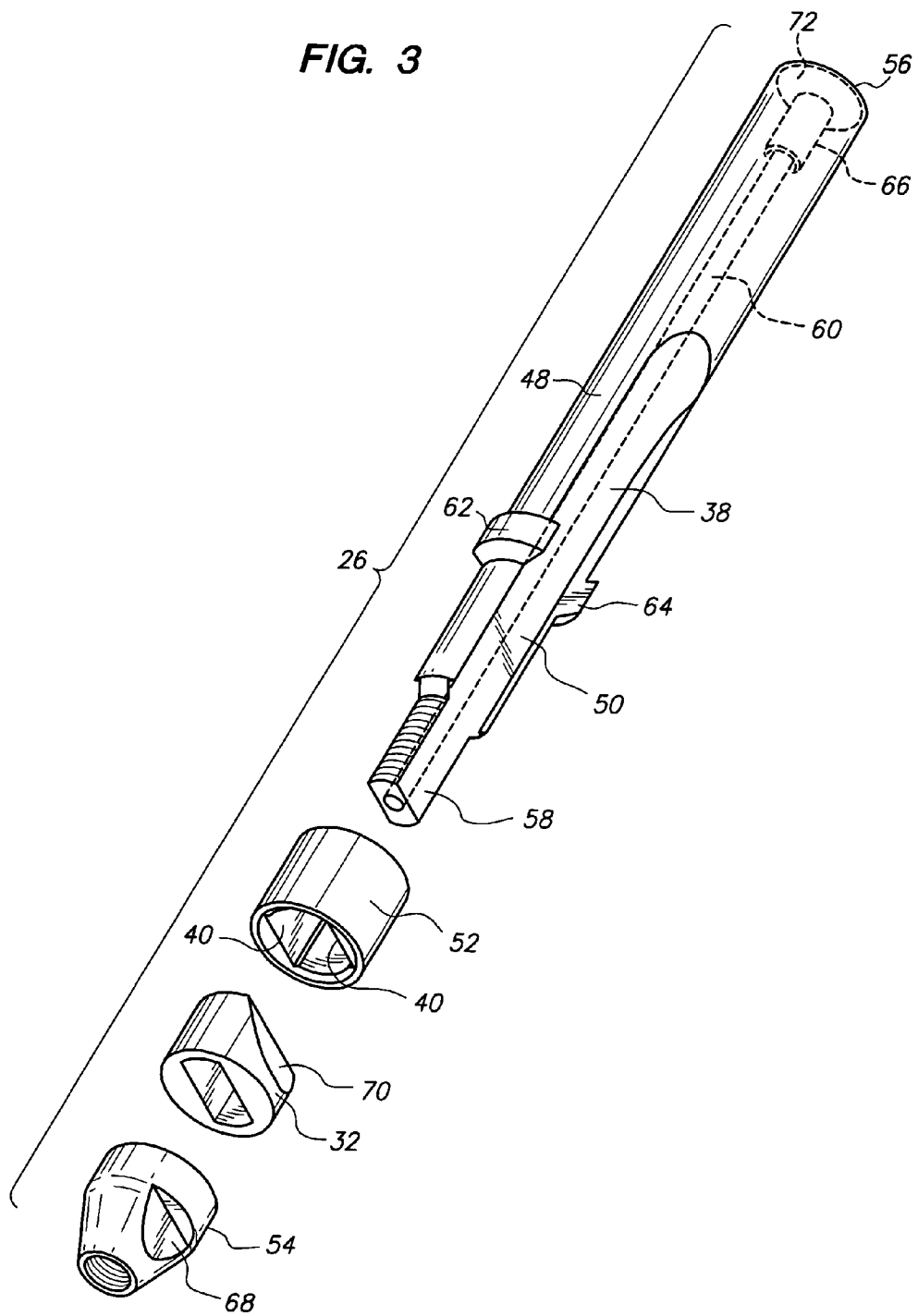
FIG. 3 is an exploded view of the segment guiding means.

FIG. 3 is an exploded view of the segment guiding means at the distal end of the nail sheath 36. In FIG. 3 and in detail in FIGS. 4 to 11, the segment guiding means 26 is shown with a core 48, longitudinal channel floors 50, and segment guiding channels 40 comprising a channel enclosing sleeve 52, a segment deflecting sleeve 32 and a conical end nut 54. The core 48 comprises an elongate generally cylindrical rod with a proximal end 56 comprising a means 66 for the releasable attachment of a shaft 76 of a setting tool (not shown) and a distal end 58 which is threaded, and which is centrally cannulated throughout its length to enable the use of a guide wire, (not shown). The proximal end of the core 56 is dimensioned for a sliding fit within the distal sheath lumen 28. A circumferential collar 62 between the proximal and distal end of the core 58 limits the extent of proximal translation of members 52, 32, and 54. The core also comprises openings in the collar 62 to allow the sheath segments 22 to pass through it. The distal end of the core is threaded to accept the similarly threaded conical end nut 54.

Figure 9:
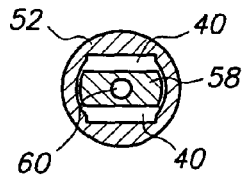
FIG. 9 is a cross-sectional view along line 9 in FIG. 5.

The approximately distal half of the core comprises a plurality of elongate flat bottomed grooves 38 that comprise the channel floors 50 of the segment guiding channels 40. There are two radially opposed channels in a preferred embodiment. The channel enclosing sleeve 52 and the segment deflecting sleeve 32 are dimensioned for a sliding fit over the distal core, and both are held tightly against the collar 62 by the conical threaded end nut 54. The end nut comprises two wrench flats 68. The channel enclosing sleeve 52 comprises an elongate hollow cylinder composed of a biocompatible material or alloy with high tensile strength. FIG. 9 shows the interior profile of the channel enclosing sleeve which creates segment guiding channels 40 for the sheath segments 22 to pass through, with the flattened section of the core forming the floor of the channel 50.

Figure 4:
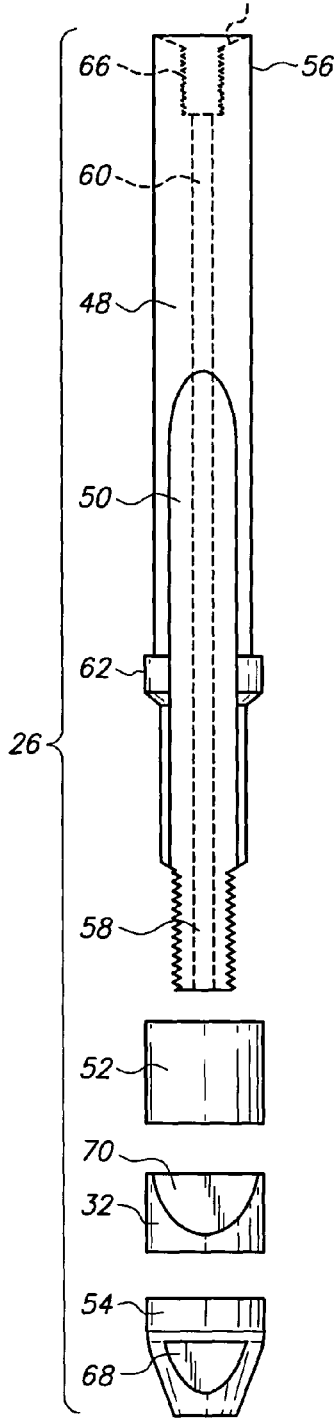
FIG. 4 is a frontal exploded view of the segment guiding means with two segment guiding channels, placed adjacent to the fully assembled means in FIG. 5 to show the relationship of the parts.
Figure 5:
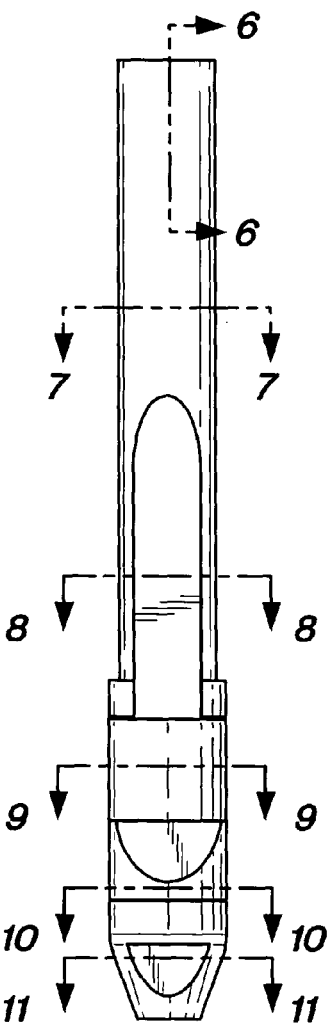
FIG. 5 is a frontal view of the fully assembled segment guiding means with two segment guiding channels and with cross-sections indicated.
Figure 10:
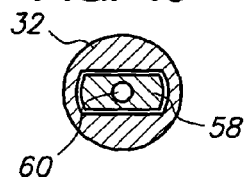
FIG. 10 is a cross-sectional view along line 10 in FIG. 5.

The proximal end of the segment deflecting sleeve 32 shown in FIGS. 3,4, and 5 and in section in FIG. 10, comprises two bevels 30 in the preferred embodiment, each bevel adjacent to the exit orifice of the segment channels 40. The bevels deflect the sheath segments as they exit the segment guiding channels.

In an embodiment in which the number of distal sheath segments is three, (not shown) the core 48 of the segment guiding means is trihedral and with three channel floors, three channels, and a segment deflecting sleeve with three bevels.

Figure 6:
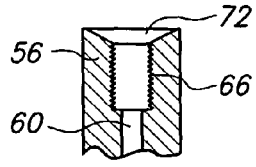
FIG. 6 is a longitudinal cross section along line 6 of the end of the segment guiding means.

FIG. 6 is a longitudinal sectional view of the proximal end of the segment guiding means 56, showing the central guide wire channel 60, and the threaded means 66 for the releasable attachment of the shaft 76 of a setting tool, (not shown). The inlet of the threaded means is chamfered 72

Figure 7:
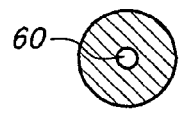
FIG. 7 is a cross-sectional view along line 7 in FIG. 5.

FIG. 7 is a cross-sectional view through the proximal end of the core 48 of the segment guiding means 56. It is dimensioned for a sliding fit within the nail sheath 34 and is cannulated 60, for a guide wire, as also shown in FIGS. 8-11.

Figure 8:
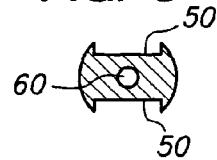
FIG. 8 is a cross-sectional view along line 8 in FIG. 5.

FIG. 8 is a cross-sectional view of the segment guiding means at the level of the elongate grooves 38 that comprise the floors 50 of the segment guiding channels 40.

FIG. 9 is a cross-sectional view through the channel enclosing sleeve 52, and the distal end of the core 58, showing two segment guiding channels 40 in this embodiment of the nail.

FIG. 10 is a cross-sectional view through the segment deflecting sleeve 32. This section is distal to the segment deflecting bevels 30.

Figure 11:
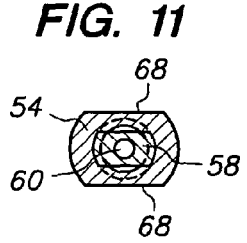
FIG. 11 is a cross-sectional view along line 11 in FIG. 5.

FIG. 11 is a cross-sectional view through the distal core 58 and the threaded conical end nut 54, showing the central guide wire channel 60 and the wrench flats 68.

FIG. 12 is a partially sectioned frontal view of the nail 10 in a narrow osseous canal 74 prior to deployment of the sheath segments 22. The segments are located within the segment guiding channels 40. A fragment of the shaft 76 of a setting tool, (not shown) is attached to the proximal end of the core 56.

FIG. 13 is a partially sectioned frontal view of the nail 10 in a narrow osseous canal 74 following the deployment of the sheath segments into hard cortical bone, 78. The shaft 76 of a setting tool (not shown) has been removed. It should be noted that the radial distal direction of the sheath segments and their embedding directly into the cortical bone tends to resist distally directed shearing and rotational forces that occur with weight bearing, as compared to transversely placed screws.

PART NAME

| | |
|---|---|
| 10 | Nail |
| 12 | Tubular bone |
| 14 | Fracture |
| 16 | Proximal end of nail |
| 18 | Distal end of nail |
| 20 | Tubular body of nail |
| 22 | Sheath segments |
| 24 | Cancellous bone |
| 26 | Segment guiding means |
| 28 | Distal nail lumen |
| 30 | Bevels of segment deflector sleeve |
| 32 | Segment deflector sleeve |
| 34 | Nail sheath |
| 36 | Distal end of nail sheath |
| 38 | Elongate grooves |
| 40 | Segment guiding channels |
| 42 | Bone penetrating cutting means |
| 44 | Screw orifices |
| 46 | Transfixing screw |
| 48 | Core of segment guiding means |
| 50 | Longitudinal channel floor |
| 52 | Channel enclosing sleeve |
| 54 | Conical end nut |
| 56 | Prox. end of core of segment guiding means |
| 58 | Distal end of core of segment guiding means |
| 60 | Central cannulation of core |
| 62 | Circumferential collar |
| 64 | Openings in collar |
| 66 | Proximal attachment means of segment guiding means |
| 68 | Wrench flats |
| 70 | Segment deflecting bevels |
| 72 | Chamfered opening |
| 74 | Narrow osseous canal |
| 76 | Shaft of setting tool |
| 78 | Hard cortical bone |

What I claim is:

1. A distal locking intramedullary nail for insertion into an intramedullary canal of a tubular bone, the intramedullary nail comprising:

an elongate generally tubular sheath, said tubular sheath comprising a proximal end and a distal end, defining a longitudinal axis therebetween, and with the distal end of said tubular sheath comprising a plurality of circumferentially equally spaced elongate segments, with each elongate segment comprising a proximal end and distal end, and with the proximal end of each elongate segment conjoined with the distal end of said tubular sheath, and with the distal end of each elongate segment positioned distally away from the distal end of said tubular sheath, and with the distal end of each elongate segment comprising a bone penetrating cutting means, said cutting means comprising a sharpened wedge-like point; and an elongate generally cylindrical segment guiding means comprising:

an elongate generally cylindrical central core having a proximal end and a distal end, and having a length measured from the proximal end of the central core to the distal end of the central core, and with said central core comprising a circumferential collar located closer to the distal end of the central core than the proximal end of the central core along the length of the central core, and with the outer diameter of the proximal end of the central core equal to the internal diameter of the tubular sheath, thereby enabling the proximal end of the central core to be positioned within the distal end of the tubular sheath, and with the proximal end of said central core comprising a means for releasable attachment of an elongate shaft of a setting tool, said means comprising a threaded orifice with a chamfered inlet, and with the distal end of the central core comprising external threads, said external threads enabling the engagement of an internally threaded end nut with the distal end of the central core, the central core further comprising a plurality of circumferentially disposed, longitudinally directed segment guiding channels, said guiding channels extending distally to the distal end of said central core from a location distal of the proximal end of the central core, with the depth and width of said guiding cannels dimensioned to enable said elongate segments of the tubular sheath to be positioned therein, the elongate segments being translatable through the guiding channels such that they are configured to exit from the guiding channels in a radial-distal direction during which time the segment guiding means is maintained in a stationary position relative to the intramedullary canal by means of said elongate shaft of said setting tool, said central core further comprising a plurality of longitudinally extending flat-bottomed grooves circumferentially spaced around the central core, said grooves forming floors of the channels;

an elongate, generally cylindrical, tubular channel-enclosing sleeve having a longitudinal axis, a proximal end, and a distal end, and having an inner lumen configured for a sliding fit over the central core at a location distal and butting up against the circumferential collar, the longitudinal axis of said channel-enclosing sleeve coaxial with the longitudinal axis of said central core;

an elongate, generally cylindrical tubular segment-deflecting sleeve having a longitudinal axis, a proximal end, and a distal end, said proximal end comprising a plurality of bevels, the longitudinal axis of said segment-deflecting sleeve coaxial with the longitudinal axis of said central core; and an elongate end nut having a longitudinal axis, a generally cylindrical proximal end, and a generally conical distal end and comprising a central threaded channel for engagement with the distal end of said central core, said end nut also including two wrench flats on an outer surface of the end nut, the longitudinal axis of said end nut coaxial with the longitudinal axis of said central core, said end nut enabling the holding of said channel-enclosing sleeve, said segment-deflecting sleeve, and said circumferential collar of said central core in close apposition to each other.

2. The intramedullary nail of claim 1, wherein the bevels of the segment-deflecting sleeve are angularly sloped to enable the deflection of said elongate segments into a radial-distal direction as the elongate segments are translated through the guiding channels.

3. The intramedullary nail of claim 1, wherein each of said elongate segments of the tubular sheath comprise two opposing, flat surfaces to facilitate positioning of the elongate segments in the guiding channels, and wherein portions of the elongate segments proximal of the channel-enclosing sleeve are bowed towards a centerline of the segment guiding means.

4. The intramedullary nail of claim 1, wherein said tubular sheath, said circumferential collar, said channel-enclosing sleeve, said segment-deflecting sleeve, and said end nut comprise a predetermined similar outer diameter.

5. The intramedullary nail of claim 1, wherein said plurality of elongate segments, said plurality of guiding channels, and said plurality of bevels are each two in number.

6. The intramedullary nail of claim 1, wherein said central core is cannulated.

7. A method of fixation of a fracture of a shaft of an elongate tubular bone having an intramedullary canal, comprising the steps of:

a. creating an opening in one end of the intramedullary canal of said tubular bone, said opening sized to receive the intramedullary nail of claim 1;

b. inserting a guide wire distally into said opening of the intramedullary canal, c. inserting the intramedullary nail of claim 1 over a proximal end of the guide wire into the intramedullary canal, d. removing the guide wire, e. attaching an elongate shaft of a setting tool to the proximal end of said central core of said intramedullary nail of claim 1, f. urging the tubular sheath of the intramedullary nail of claim 1 distally into the intramedullary canal, thereby g. causing the elongate segments of the intramedullary nail of claim 1 to be translated distally through the guiding channels of the intramedullary nail of claim 1 such that they exit from the guiding channels in a radial-distal direction, thereby h. causing the bone penetrating cutting means of the distal end of each elongate segment to penetrate into the tubular bone, and i. detaching and removing the elongate shaft of the setting tool from the proximal end of the central core.

* * * * *